United States Patent
Baid

(10) Patent No.: US 10,265,508 B2
(45) Date of Patent: Apr. 23, 2019

(54) INTRAVENOUS CATHETER APPARATUS

(75) Inventor: Rishi Baid, New Delhi (IN)

(73) Assignee: Poly Medicure Limited, Faridabad, Haryana (IN)

( * ) Notice: Subject to any disclaimer, the term of this patent is extended or adjusted under 35 U.S.C. 154(b) by 0 days.

(21) Appl. No.: 14/356,998

(22) PCT Filed: Mar. 27, 2012

(86) PCT No.: PCT/IB2012/051457
§ 371 (c)(1),
(2), (4) Date: May 8, 2014

(87) PCT Pub. No.: WO2013/068856
PCT Pub. Date: May 16, 2013

(65) Prior Publication Data
US 2014/0343497 A1 Nov. 20, 2014

(30) Foreign Application Priority Data
Nov. 8, 2011 (IN) .......................... 3159/DEL/2011

(51) Int. Cl.
*A61M 25/06* (2006.01)
*A61M 5/32* (2006.01)

(52) U.S. Cl.
CPC ........ *A61M 25/0618* (2013.01); *A61M 5/329* (2013.01); *A61M 25/0606* (2013.01); *A61M 5/3273* (2013.01); *F04C 2270/0421* (2013.01)

(58) Field of Classification Search
CPC ................ A61M 5/3273; A61M 5/329; A61M 25/0606; A61M 25/0612; A61M 25/0618
See application file for complete search history.

(56) References Cited

U.S. PATENT DOCUMENTS

| 7,604,616 B2 * | 10/2009 | Thoresen | A61M 5/3273 604/164.08 |
| 2005/0277879 A1 | 12/2005 | Daga | |
| 2010/0222749 A1 * | 9/2010 | Baid | A61M 5/3273 604/263 |
| 2010/0241087 A1 * | 9/2010 | Moulton | A61M 25/0618 604/263 |

FOREIGN PATENT DOCUMENTS

| EP | 2 016 963 A1 | 1/2009 |
| WO | WO 2009/116080 A2 | 9/2009 |
| WO | WO 2011/036574 A1 | 3/2011 |

OTHER PUBLICATIONS

International Search Report; International Application No. PCT/IB2012/051457; dated Jun. 18, 2012; 3 pages.

* cited by examiner

*Primary Examiner* — Nathan R Price
*Assistant Examiner* — Justin L Zamory
(74) *Attorney, Agent, or Firm* — C. John Brannon; Brannon Sowers & Cracraft PC

(57) ABSTRACT

The invention relates to an intravenous catheter apparatus comprising a catheter hub arranged at a proximal end of a catheter tube, the catheter hub having an inner surface defining a chamber; a needle having a needle tip at its distal end and extending through the chamber and the catheter tube when in a ready position; and a needle guard slidably arranged on the needle and received in the chamber when the needle is in its ready position, wherein the needle guard is configured to guard the needle tip upon withdrawal of the needle from the catheter hub.

16 Claims, 5 Drawing Sheets

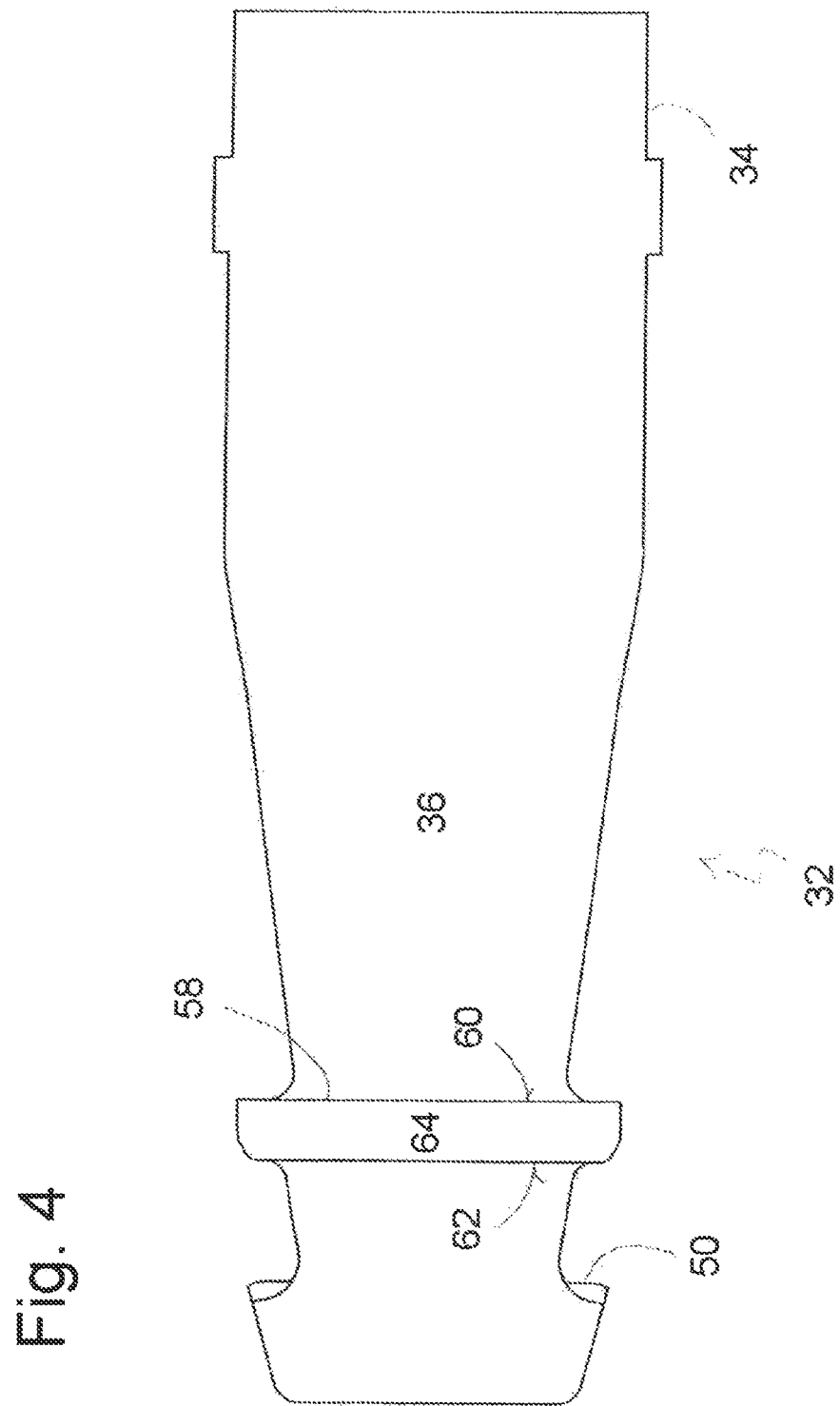

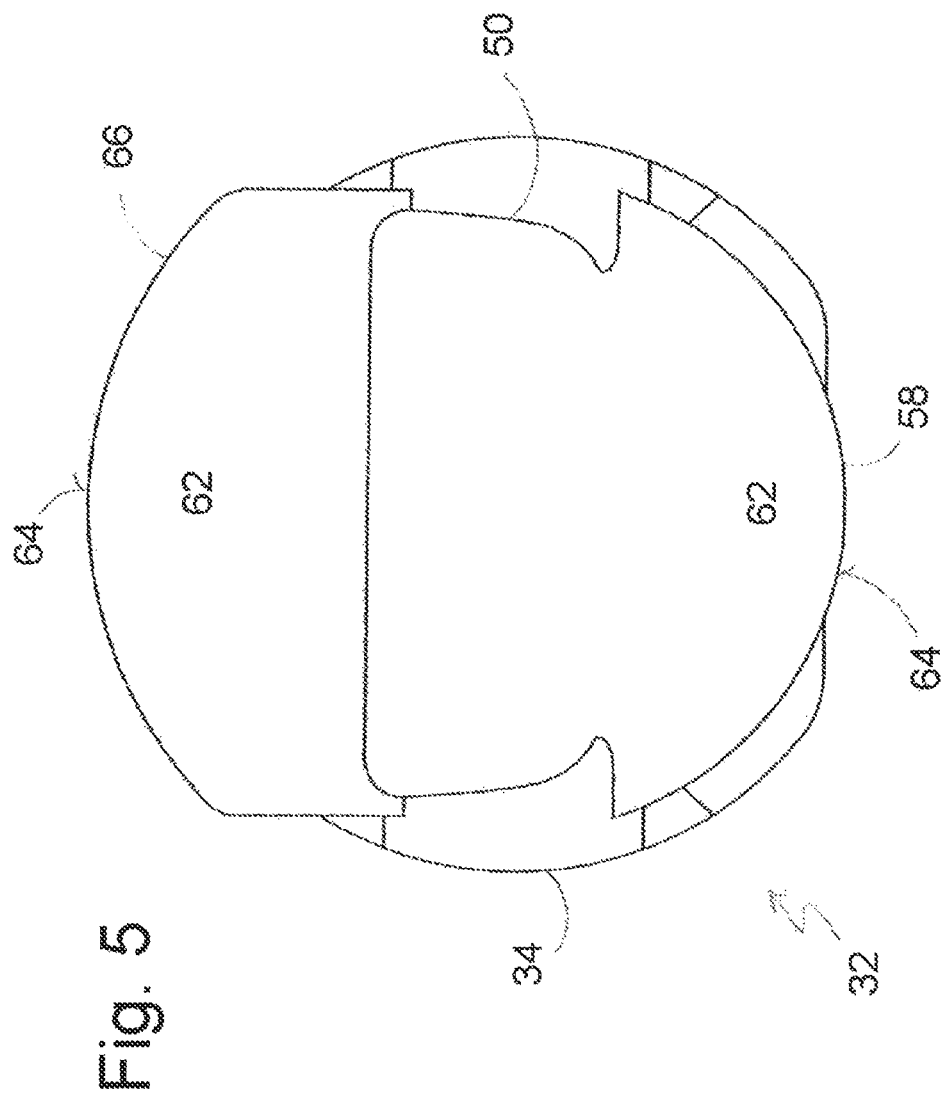

INTRAVENOUS CATHETER APPARATUS

RELATED APPLICATION INFORMATION

This application is a U.S. National Phase of International PCT Application No. PCT/GB2011/052554 filed on Dec. 22, 2011, which claims priority to and the benefit of Indian provisional Patent Application No. 3159/DEL/2011 filed on Nov. 8, 2011. The entire contents of each application is incorporated herein by reference.

The invention relates to an intravenous catheter apparatus comprising a catheter hub arranged at a proximal end of a catheter tube and having an inner surface defining a chamber; a needle having a needle tip and extending through the chamber and the catheter tube when in a ready position; and a needle guard slidably arranged on the needle and received in the chamber when the needle is in its ready position, wherein the needle guard is configured to guard the needle tip upon withdrawal of the needle from the catheter hub.

An intravenous catheter apparatus of this kind is generally known. The needle guard serves to prevent a person handling the intravenous catheter apparatus from accidentally coming into contact with the needle tip after placement of the catheter tube in and subsequent removal of the needle from a patient's vein. Thereby, the intravenous catheter apparatus helps to avoid unwanted transmission of blood borne diseases.

It is an object of the present invention to provide an intravenous catheter apparatus which provides better protection against accidental pricking by the needle tip and which is inexpensive to manufacture at the same time.

The object is satisfied by an intravenous catheter apparatus in accordance with claim 1.

The intravenous catheter apparatus of the invention comprises a catheter hub arranged at a proximal end of a catheter tube and having an inner surface defining a chamber; a needle defining an axial direction and having a needle tip, wherein the needle extends through the chamber and the catheter tube when in a ready position; a needle guard slidably arranged on the needle and received in the chamber when the needle is in its ready position, the needle guard including a base portion and first and second arms extending from the base portion, wherein the first arm is deflected radially outwards by the needle against a restoring force when the needle is in its ready position whereby the needle guard is brought into retaining contact with the catheter hub; and retaining means for retaining the needle guard in the chamber as long as the first arm is in its deflected state. The retaining means include a first disc-like retaining protrusion provided on the first arm and a retaining depression formed in the inner surface of the catheter hub and adapted to receive the retaining protrusion.

The disc-like retaining protrusion has the benefit that it is engagement along a circular contact surface with the corresponding retaining depression formed in the inner surface of the catheter hub. Differing from IV catheter apparatuses as known from the prior art, this provides an engagement between the needle guard and the catheter hub along a substantial annular portion of the retaining protrusion and the retaining depression which provides a safe and reliable engagement between the two components as long as the needle guard is in its ready position and is to be prevented from being retracted out of the needle hub. Even if the needle guard is rotated within the catheter hub, this secure engagement between the catheter hub and the needle guard holds the needle guard safely within the catheter hub.

Because of a depression being formed in the inner surface of the catheter hub for retaining the needle guard in the chamber, instead of e.g. a protrusion, the catheter hub can be manufactured more easily and, thus, at less manufacturing cost, in particular if the catheter hub is a plastic part and e.g. formed by injection molding. At the same time the particular design of the first retaining protrusion provided on the needle guard ensures effective engagement of the retaining protrusion with the retaining depression and, thus, reliable retaining of the needle guard in the catheter hub. Hence, the risk of premature release of the needle guard from the catheter hub during withdrawal of the needle from the catheter hub and, thus, the risk of accidental pricking by the needle is reduced.

According to a preferred embodiment, the retaining protrusion is of part-circular, in particular semi-circular shape. More specifically, the retaining protrusion may have generally parallel proximal and distal faces and/or a convex, in particular part-cylindrical, peripheral surface.

According to another embodiment, the first retaining protrusion is arranged in the region of a distal end of the first arm.

According to yet another embodiment, a second disk-like retaining protrusion is arranged on the second arm and adapted to engage with the retaining depression as long as the first arm is in its deflected state.

According to yet another embodiment, the second arm can be deflected along its entire length radially inwards when the needle tip is received between the arms, to thereby allow the second retaining protrusion to disengage from the retaining depression.

According to yet another embodiment, the second retaining protrusion is arranged in the region of a distal end of the second arm. In particular, the second retaining protrusion may be arranged opposite from the first retaining protrusion.

According to yet another embodiment, the retaining depression is an at least part-annular depression, preferably an annular depression.

According to yet another embodiment, the restoring force is created by at least one of an elastic property of the first arm and an additional tension element. For example, the needle guard may comprise a tension element at least partly surrounding the arms in a region proximal of the first retaining protrusion or—instead of surrounding the two arms—biasing the two arms by a linear biasing action. Alternatively or additionally, the first and second arms can be made of a resilient material.

According to yet another embodiment, the first and second arms are made of a plastic material. Preferably, the first and second arms are integrally formed with the base portion also made of a plastic material, e.g. by injection molding.

According to yet another embodiment, the needle comprises an engagement means provided at a distance from the needle tip for engaging with the needle guard and preventing the needle guard from sliding off the needle. Preferably, the engagement means is formed of by enlargement of the radial dimension of the needle in at least one direction as compared with a principal profile of the needle. The engagement means can be found by a local crimp, a shoulder, a bulge formed as an annular widening etc.

According to yet another embodiment, the needle guard comprises a stopping element engaging with the engagement means of the needle when the needle tip is received between the first and second arms. Preferably, the stopping element defines an axial bore having a cross-section adapted to the principal profile of the needle but being smaller than the enlargement of the needle. Furthermore, the stopping element may be made of a material different from the material of the base portion, in particular of a metal material. The stopping element may be of disc-like shape or tubular shape and/or arranged on a distal side of the base portion. It can be fixed in the base portion or supported in a floating manner on the needle.

A preferred embodiment of the invention will now be described by way of example only with reference to the accompanying drawings.

FIG. 4 is a bottom view of the needle guard of FIG. 2; and

FIG. 5 is a front view of a distal end of the needle guard of FIG. 2.

Figure 1:
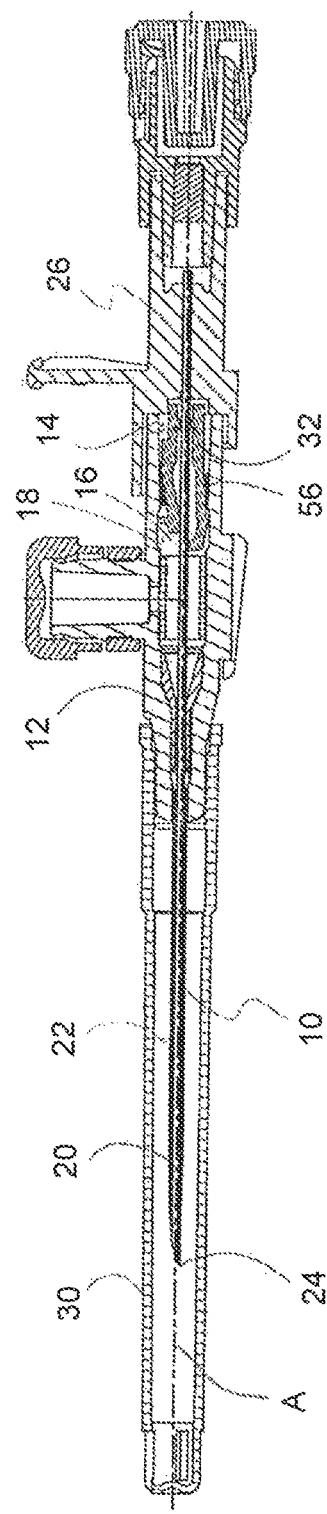
FIG. 1 is a longitudinal sectional view of an intravenous catheter apparatus of the invention.

FIG. 1 shows an intravenous catheter apparatus comprising a catheter tube 10 and a catheter hub 12 attached to the catheter tube 10 at a proximal end thereof. It will be appreciated that the term 'proximal' refers to a position or orientation close to a person handling the intravenous catheter apparatus whereas the term 'distal' refers to a position or orientation distant from this person, wherein the longitudinal direction A of a needle 20 is the reference direction.

The catheter hub 12 has an inner surface 14 which defines a chamber 16 of generally circular cross-section. The chamber 16 is located in a proximal section of the catheter hub 12. In a distal region of the chamber 16 the inner surface 14 of the catheter hub is provided with an annular retaining depression 18 the function of which will be discussed in more detail further below.

The needle 20 having distal and proximal ends extends through the chamber 16 of the catheter hub 12 as well as through the catheter tube 10. The needle 20 comprises a needle shaft 22 and a needle tip 24 at its distal end. A needle hub 26 is attached to the proximal end of the needle 20. The needle 20 defines said axial (longitudinal) direction A and the needle shaft 22 has a generally constant principal profile, except for an enlargement of the radial dimension of the needle 20 in at least one direction as compared to the principal profile, which is positioned in the region of the needle tip 24 and forms an engagement means (not shown). Preferably, the engagement means is made by crimping of the needle 20. However, it could also be made by welding, milling, cold heading or expanding of the needle. The function of the engagement means will be discussed in more detail further below.

FIG. 1 shows the intravenous catheter apparatus in a condition prior to use, in which the needle 20 extends all the way through the chamber 16 of the catheter hub 12 as well as the catheter tube 10 and the needle tip 24 protrudes from a distal end of the catheter tube 10. This position of the needle 20 is also referred to as the ready position in this context. It is to be noted that the needle 20 is fixed in its ready position by the needle hub 26 engaging with the catheter hub 12.

In order to prevent accidental pricking by the needle 20 prior to use of the intravenous catheter apparatus, a tubular cover 30 covers the catheter tube 10 and the portion of the needle 20 extending therethrough. A proximal end portion of the cover 30 is removably fixed to a distal end portion of the catheter hub 12.

The intravenous catheter apparatus further comprises a needle guard 32 for protecting the needle tip 24 after use of the needle 20, i.e. after placement of the catheter tube 10 in and withdrawal of the needle 20 from a patient's vein. The needle guard 32 is slidably arranged on the needle shaft 22 and received in the chamber 16.

As can be seen in more detail in FIGS. 2 to 5, the needle guard 32 comprises a tubular base portion 34 and first and second arms 36, 38 extending from a distal side of the tubular base portion 34 generally in the axial direction. The base portion 34 and the arms 36, 38 are integrally made of a plastic material, for example by injection molding.

The base portion 34 has an axial through-bore 40 for receiving the needle 20. The through-bore 40 comprises first and second sections 42, 44 both having cross-sections that are larger than the principal profile of the needle 20, the cross-section of the second section 44 being even larger than the cross-section of the first section 42.

A stopping element 46 in the shape of a disk-like plate, such as a washer, is arranged at the distal side of the base portion 34, for example by insert molding. The stopping element 46 is made of a material different from the material of the base portion 34, for example of a metal material. The stopping element 46 has an axial bore 48 which is aligned with the through-bore 40 of the base portion 34 and which has a cross-section which is smaller than that of the through-bore 40 of the base portion 34. More specifically, the cross-section of the axial bore 48 of the stopping element 46 is adapted to the principal profile of the needle 20 such that the stopping element 46 can slide along the needle shaft 22 with minimum friction. However, a maximum dimension of the axial bore 48 transverse to the longitudinal direction A is smaller than a maximum dimension of the engagement means provided on the needle 20 transverse to the longitudinal direction so as to prevent the engagement means from passing through the stopping element 46 and, thus, to prevent the needle guard 32 from sliding off the needle 20.

Figure 2:
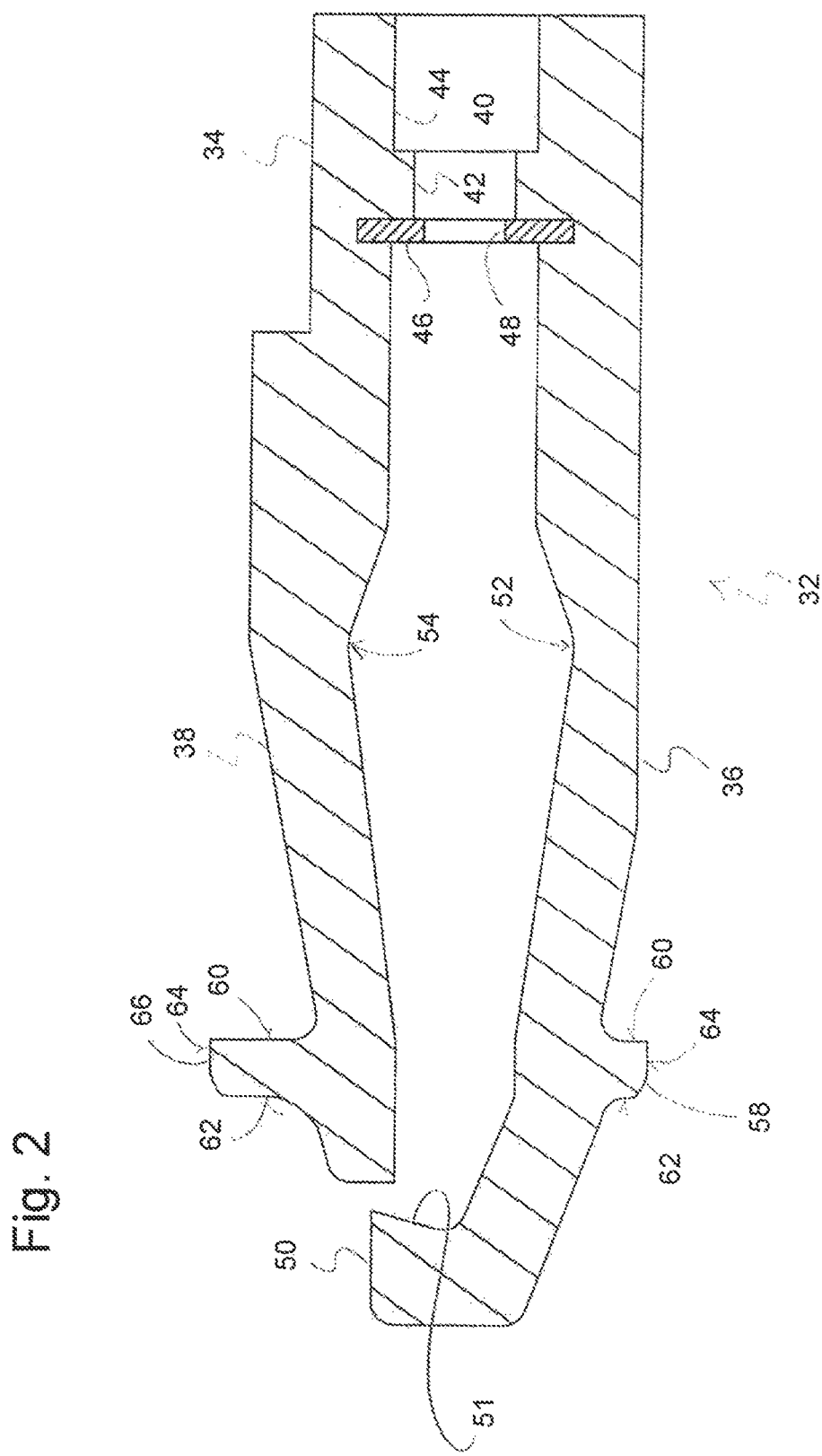
FIG. 2 is a longitudinal sectional view of a needle guard of the intravenous catheter apparatus of FIG. 1 without a tension element.
Figure 3:
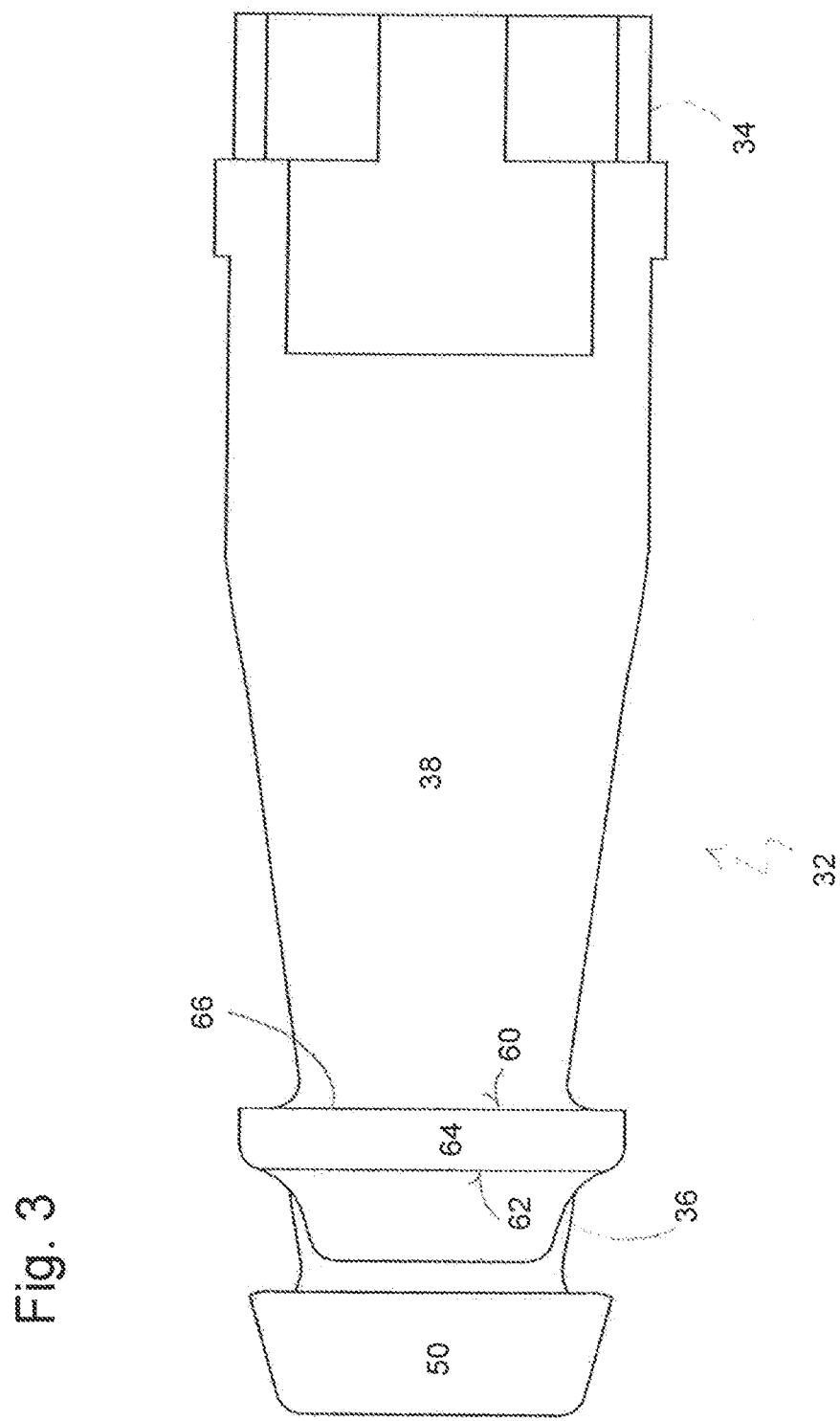
FIG. 3 is a top view of the needle guard of FIG. 2.

The first arm 36 of the needle guard 32 is longer than the second arm 38 and has a massive distal end section 50 having an undercut 51 for catching the needle tip 24. The distal end section 50 is angled towards the second arm 38 and overlaps with the second arm 38 (FIG. 2). In its ready position the needle 20 extends completely through the needle guard 32 (FIG. 1). In this situation the distal end section 50 of the first arm 38 is supported on the needle shaft 22 thereby deflecting the first arm 36 radially outwards. In order to facilitate deflection of the first arm 36, the first arm 36 has a narrowed portion 52 of reduced cross-section approximately in a middle region of the arm 36. In contrast to the first arm 36 and because of a lack of angled distal end section, the second arm 38 is not significantly deflected by the needle 20 extending through the needle guard 32. Nonetheless, the second arm 38 has a similar narrowed portion 54 the reason for which will become apparent further below.

Even though the first and second arms 36, 38 have certain elastic properties, a tension element, for example a rubber band 56, surrounds a distal section of the arms 36, 38 such that deflection of the first arm 36 occurs mainly against a restoring force of the tension element (FIG. 1).

When the needle 20 is withdrawn from the catheter tube 10 after placement of the catheter tube 10 in a patient's vein, the needle 20 slides though the needle guard 32 until the needle tip 24 passes the angled distal end section 50 of the first arm 36. At this point the angled distal end section 50 is no longer supported on the needle shaft 22 and the first arm 36—mainly by force of the rubber band 56—snaps back into its relaxed state with the angled distal end section 50 now blocking the needle tip 24. It will be appreciated that the length of the first arm 36 and the distance of the engagement means from the needle tip 24 are adapted to each other such that the needle tip 24 received in the needle guard 32 has a minimum of clearance with respect to axial movement in the needle guard 32.

In order to prevent the needle guard 32 from being prematurely removed from the chamber 16 of the catheter hub 12, i.e. before the needle tip 24 is covered by the needle guard 32, the first arm 36 is provided with a disc-like first retaining protrusion 58 engaging with the retaining depression 18 in the inner surface 14 of the catheter hub 14 in the deflected state of the first arm 36. The first retaining protrusion 58 has generally flat proximal and distal faces 60, 62 and a convex, in particular part-cylindrical, peripheral surface 64 the radius of which is adapted to the radius of the inner surface 14 of the catheter hub 12 in the region of the retaining depression 18. The height of the first retaining protrusion 58, i.e. its dimension seen in the radial direction, is adapted such that the first retaining protrusion 58 disengages from the retaining depression 18 when the first arm 36 snaps back into its relaxed state.

The second arm 38 is provided with a disc-like second retaining protrusion 66 which is similar to the first retaining protrusion 58 and which extends in a radial direction opposite from the first retaining protrusion 58. The second retaining protrusion 66 also has generally parallel proximal and distal faces 60, 62 as well as a convex, in particular part-cylindrical, peripheral surface 64. The height of the second retaining protrusion 66, i.e. its dimension seen in the radial direction, is adapted such that the retaining protrusion 66 engages with the retaining depression 18 when the needle 20 is in its ready position. In order to disengage the retaining protrusion 66 from the retaining depression 18, the second arm 38 can be deflected slightly radially inwards towards the needle 20 when the pulling force on the needle 20 becomes great enough.

As can be seen from FIG. 1, the axial dimension, i.e. width, of the retaining depression 18 is significantly larger than the axial dimension, i.e. width, of the retaining protrusions 58, 66. For example, the width of the retaining depression 18 can be three to five times the width of the retaining protrusions 58, 66, although other ratios are possible as long as reliable engagement between the retaining depression 18 and the retaining protrusions 58, 66 is ensured.

REFERENCE NUMERALS 10 catheter tube
12 catheter hub
14 inner surface
16 chamber
18 retaining depression
20 needle
22 needle shaft
24 needle tip
26 needle hub
30 tubular cover
32 needle guard
34 base portion
36 first arm
38 second arm
40 through-bore
42 first section
44 second section
46 stopping element
48 axial bore
50 distal end section
51 undercut
52 narrowed portion
54 narrowed portion
56 rubber band
58 retaining protrusion
60 proximal face
62 distal face
64 peripheral surface
66 retaining protrusion
A longitudinal direction

The invention claimed is:

1. An intravenous catheter apparatus comprising:
a catheter hub arranged at a proximal end of a catheter tube, the catheter hub having an inner surface defining a chamber;
a needle defining an axial direction and having a needle tip, the needle extending through the chamber and the catheter tube when in a ready position;
a needle guard slidably arranged on the needle and received in the chamber when the needle is in the ready position, the needle guard including a base portion and first and second arms extending from the base portion, the base portion and the arms being integrally made of a plastic material wherein the first arm includes a centrally-positioned narrowed portion of reduced cross-section for facilitating deflection and is deflected radially outwards by the needle against a restoring force when the needle is in the ready position whereby the needle guard is brought into retaining contact with the catheter hub; and
a retainer for retaining the needle guard in the chamber as long as the first arm is in its deflected state, the retainer including a first disc-like retaining protrusion provided on the first arm and an annular retaining depression formed in the inner surface of the catheter hub and adapted to receive the retaining protrusion, wherein the retaining protrusion has generally parallel proximal and distal faces, wherein the needle guard comprises a stopping element made of a metal material for engaging with an engagement means of the needle when the needle tip is received between the arms, to thereby prevent the needle guard from sliding off the needle, the stopping element being arranged on a distal side of the base portion, wherein the stopping element is supported in a floating manner on the needle; and wherein the stopping element prevents proximal motion while allowing distal motion of the needle;
wherein the retaining protrusion has generally flat proximal and distal faces and a convex peripheral surface defining a first radius, the first radius being adapted to a second radius defined by the inner surface of the catheter hub to facilitate retaining engagement thereof.

2. The intravenous catheter apparatus of claim 1, wherein the retaining protrusion has a convex, in particular part-cylindrical, peripheral surface.

3. The intravenous catheter apparatus of claim 1, wherein the first retaining protrusion is arranged in the region of a distal end of the first arm.

4. The intravenous catheter apparatus of claim 1, wherein a second disk-like retaining protrusion is arranged on the second arm and adapted to engage with the retaining depression.

5. The intravenous catheter apparatus of claim 4, wherein the second arm can be deflected radially inwards when the needle tip is received between the arms, to thereby allow the second disc-like retaining protrusion to disengage from the retaining depression.

6. The intravenous catheter apparatus of claim 4, wherein the second disc-like retaining protrusion is arranged in the region of a distal end of the second arm.

7. The intravenous catheter apparatus of claim 4, wherein the second disk-like retaining protrusion is arranged opposite from the first retaining protrusion.

8. The intravenous catheter apparatus of claim 1, wherein the retaining depression is an at least part-annular depression, preferably an annular depression.

9. The intravenous catheter apparatus of claim 1, wherein the restoring force is created by at least one of an elastic property of the first arm and an additional tension element at least partly surrounding the arms.

10. The intravenous catheter apparatus of claim 1, wherein the needle guard comprises a tension element at least partly surrounding the arms in a region proximal of the first retaining protrusion or applying a linear biasing force biasing the arms together.

11. The intravenous catheter apparatus of claim 1, wherein the stopping element defines an axial bore having a cross-section adapted to a principal profile of the needle but being smaller than a maximum radial dimension of the engagement means.

12. The intravenous catheter apparatus of claim 1, wherein the stopping element is of disc-like shape.

13. The intravenous catheter apparatus of claim 1, wherein the stopping element is arranged on a distal side of the base portion.

14. The intravenous catheter apparatus of claim 1, wherein the engagement means is formed by an enlargement of the radial dimension of the needle in at least one direction as compared with a principal profile of the needle.

15. An intravenous catheter apparatus comprising:
a catheter hub arranged at a proximal end of a catheter tube, the catheter hub having an inner surface defining a chamber;
a needle defining an axial direction and having a needle tip, the needle extending through the chamber and the catheter tube when in a ready position;
a needle guard slidably arranged on the needle and received in the chamber when the needle is in the ready position, the needle guard including a base portion and first and second arms extending from the base portion, the first arm including a first narrowed portion of reduced cross-section for facilitating deflection and located about midway from the base portion and the second arm including a second narrowed portion of reduced cross-section and located about midway from the base portion, the base portion and the arms being integrally made of a single plastic material wherein the first arm is deflected radially outwards by the needle against a restoring force when the needle is in the ready position whereby the needle guard is brought into retaining contact with the catheter hub; and
a retainer for retaining the needle guard in the chamber as long as the first arm is in its deflected state, the retainer including a first disc-like retaining protrusion provided on the first arm and an annular retaining depression formed in the inner surface of the catheter hub and adapted to receive the retaining protrusion, wherein the retaining protrusion has generally parallel proximal and distal faces, wherein the needle guard comprises a stopping element for preventing proximal motion of the needle while allowing distal motion of the needle, and made of a metal material for engaging with an engagement means of the needle when the needle tip is received between the arms, to thereby prevent the needle guard from sliding off the needle, the stopping element being arranged on a distal side of the base portion and the base portion having an axial through-bore for receiving the needle, the through-bore comprising first and second sections both having cross-sections that are larger than the principal profile of the needle, the cross-section of the second section being larger than the cross-section of the first section;
wherein the retaining protrusion has generally flat proximal and distal faces and a convex peripheral surface defining a first radius, the first radius being adapted to a second radius defined by the inner surface of the catheter hub to facilitate retaining engagement thereof; and
wherein the retaining protrusion is sized such that the retaining protrusion disengages from the retaining depression when the first arm transitions from its deflected state back to an undeflected state.

16. A catheter assembly, comprising:
a catheter tube having oppositely disposed proximal and distal ends;
a catheter hub arranged at the proximal end of the catheter tube, wherein the catheter hub has an inner surface defining a chamber;
a needle having a needle tip, wherein the needle is positioned to extend through the chamber and the catheter tube to define a ready position;
a needle guard slidably connected to the needle and further comprising:
a base portion having a proximal side and an oppositely disposed distal side; and
a first arm extending from the base portion and having a narrowed middle region for facilitating deflection of the first arm;
a second arm extending from the base portion; and
a stopping member disposed on the distal side of the base portion for preventing the needle guard from disengaging the needle when the needle tip is received between the arms;
wherein the stopping member allows distal movement while preventing proximal movement;
wherein the stopping member is supported in a floating manner on the needle;
wherein the first arm is deflected radially outwards by the needle against a restoring force when the needle is in the ready position whereby the needle guard is brought into retaining contact with the catheter hub; and
wherein the needle guard is received in the chamber when the needle is in the ready position; and
a retainer for retaining the needle guard in the chamber as long as the first arm is in its deflected state, the retainer further comprising:
a first disc-like retaining protrusion provided on the first arm; and
an annular retaining depression formed in the inner surface of the catheter hub for receiving the first disc-like retaining protrusion;
wherein the retaining protrusion has generally parallel proximal and distal faces and a convex peripheral surface portion contoured to retainingly engage the annular retaining depression.

* * * * *